(12) United States Patent
Sorensen (10) Patent No.: US 9,926,611 B2
(45) Date of Patent: Mar. 27, 2018

(54) BRAN MODIFICATION

(75) Inventor: Jens Frisbaek Sorensen, Århus N (DK)

(73) Assignee: DuPont Nutrition Biosciences ApS, Copenhagen (DK)

( * ) Notice: Subject to any disclaimer, the term of this patent is extended or adjusted under 35 U.S.C. 154(b) by 20 days.

(21) Appl. No.: 13/640,077

(22) PCT Filed: Apr. 8, 2011

(86) PCT No.: PCT/EP2011/055502
§ 371 (c)(1),
(2), (4) Date: Oct. 9, 2012

(87) PCT Pub. No.: WO2011/124678
PCT Pub. Date: Oct. 13, 2011

(65) Prior Publication Data
US 2013/0045304 A1 Feb. 21, 2013

Related U.S. Application Data

(60) Provisional application No. 61/323,098, filed on Apr. 12, 2010.

(30) Foreign Application Priority Data

Apr. 9, 2010 (EP) .................................. 10159546

(51) Int. Cl.
| | | |
|---|---|---|
| *A23L 1/105* | (2006.01) | |
| *A21D 8/04* | (2006.01) | |
| *A21D 13/06* | (2017.01) | |
| *A23L 1/164* | (2006.01) | |
| *C12N 9/42* | (2006.01) | |
| *A23L 7/10* | (2016.01) | |
| *A23L 7/104* | (2016.01) | |

(52) U.S. Cl.
CPC ....... *C12Y 302/01008* (2013.01); *A23L 7/107* (2016.08); *A23L 7/115* (2016.08); *C12Y 302/01004* (2013.01); *C12Y 302/01015* (2013.01); *C12Y 302/01021* (2013.01); *C12Y 302/01055* (2013.01); *C12Y 302/01089* (2013.01); *C12Y 302/01091* (2013.01)

(58) Field of Classification Search
CPC ........ A23L 1/1016; A23L 1/1055; A23L 1/16; A23L 1/105; A23L 1/034; A23L 1/10; A23L 1/05; A23L 1/164; A23L 1/0153; C12N 9/248; C12N 9/24; C12N 9/16; C12N 9/42; A21D 13/02; A21D 8/042; A21D 13/06; A21D 13/08; A21D 2/36; A21D 13/062; A23D 8/04; C12C 5/02; A23J 1/12; C12Y 302/01008; C12Y 302/01021; C12Y 302/01091; C12Y 302/01003; A23K 1/1656; C12F 3/10; A23C 8/04

USPC ......... 426/31, 618, 442, 549, 620, 557, 556, 426/592, 61, 52, 289, 293, 302, 303, 99, 426/18, 196, 200, 209; 435/196, 200, 435/209; 514/54

See application file for complete search history.

(56) References Cited

U.S. PATENT DOCUMENTS

| | | | |
|---|---|---|---|
| 2005/0089602 A1* | 4/2005 | Kvist et al. | .................... 426/52 |
| 2010/0040736 A1* | 2/2010 | Van Haesendonck | . A21D 13/02 426/61 |

FOREIGN PATENT DOCUMENTS

| | | |
|---|---|---|
| CN | 1871942 A | 12/2006 |
| EP | 0577294 A2 | 1/1994 |
| JP | 06070720 A | 3/1994 |
| WO | 02/067698 A1 | 9/2002 |
| WO | WO 2002/067698 A1 | 9/2002 |

OTHER PUBLICATIONS

FR-2-874-930—English Abstract.*
Neudoerffer, T. S. et al. Can. J. Animal Sci. 1969. 49: 205-2014.*
Pinnavaia, G. et al. Starch/Starke. 50: 64-67 (1998).*
Sun, X. et al. 2008. Appl. Biochem. Biotechnol. 146: 119-128.*
Santala, O. et al. J. Cereal Sci. 54 (2011) 187-194.*
Grigelmo-Miguel, Nuria et al., "Comparison of Dietary Fibre from By-products of Processing Fruits and Greens and from Cereals," Lebensm.-Wiss. u.-Technol., 1999, 32, 503-508, Academic Press.
Hu, Ye-Bi, et al., "Treatment of corn bran dietary fiber with xylanase increases its ability to bind bile salts, in vitro," Food Chemistry, 2008, 106, 113-121, Elsevier Ltd.
Rasco, B.A., et al., "Evaluation of Enzyme and Chemically Treated Wheat Bran Ingredients in Yeast-Raised Breads," Cereal Chemistry, 1991, 68(3), 295-299, American Association of Cereal Chemists, Inc.

* cited by examiner

Primary Examiner — Hamid R Badr (57) ABSTRACT

The present invention relates to a method for the modification of cereal bran, a method for the production of a modified cereal bran product as well as the use of such products in the production of food products.

15 Claims, 5 Drawing Sheets

BRAN MODIFICATION

CROSS-REFERENCE TO RELATED APPLICATIONS

This application claims priority to PCT Application No. PCT/EP2011/055502 entitled "Bran Modification," filed Apr. 8, 2011, which claims priority to U.S. Provisional Application No. 61/323,098, filed Apr. 12, 2010 and EP Application No. 10159546.0, filed Apr. 9, 2010 all of which are expressly incorporated by reference herein in their entirety.

FIELD OF THE INVENTION

The present invention relates to a method for the modification of cereal bran, a method for the production of a modified cereal bran product as well as the use of such products in the production of food products.

BACKGROUND OF THE INVENTION

Sugar beat pulp, upgraded to a commercial product, e.g. "Fibrex", can be used as water binder in several food products, e.g. including all types of bread from French bread to darker wholemeal products, cookies and biscuits, crisprolls and rusks, soft bread, flat bread and pizzas.

However, the utilization of side-streams from processing of cereal bran from milling or Distillers dried spent grain with solubles (DDGS) has received little attention beyond use in animal feeds.

EP0338787 relates to the production of enzyme-treated low-moisture content comestible products such as, for example, cookies, crackers, biscuits, snacks, cocoa, flour, plant protein extracts, hot cereals, and ready-to-eat cereals. This Invention also relates to hemicellulose hydrolyzate products.

WO02/067698 relates to a process for the extraction of soluble proteins, non-starch carbohydrates, and optionally oils from commercially available cereal bran.

There is a need in the art for better utilisation of the cereal, wherein less of the cereals will go to low price applications like cattle feed. Furthermore, it is a long felt need for being able to increase the water-binding properties of cereal bran for easier utilisation of the bran side-stream fractions in the food industry, and to make it possible to increase the health and nutritional effect of already existing products.

OBJECT OF THE INVENTION

It is an object of embodiments of the invention to provide a method for increasing the water holding capacity (WHC) of a cereal bran fraction without need for concomitantly addition of large amounts of water to the cereal bran fraction.

SUMMARY OF THE INVENTION

It has been found by the present inventor(s) that the water holding capacity (WHC) of a cereal bran fraction may be increased significantly by the addition of a cell-wall modifying enzyme to a cereal bran fraction, in which the total water content in this cereal bran fraction is lower than 100% (w/w).

So, in a first aspect the present invention relates to a method for increasing the water holding capacity (WHC) of a cereal bran fraction, said method comprising the steps of:

a) Addition of water to a particulate cereal bran fraction to obtain a water content lower than 100% (w/w);
b) Treating said particulate cereal bran fraction with added water without the removal of any components with: one or more cell-wall modifying enzyme; and optionally simultaneously or sequentially in any order treating said particulate cereal bran fraction with one or more further enzyme.

In a second aspect the present invention relates to a cereal bran fraction with increased WHC produced by a method comprising the steps of:

a) Addition of water to a particulate cereal bran fraction to obtain a water content lower than 100% (w/w);
b) Treating said particulate cereal bran fraction with added water without the removal of any components with: one or more cell-wall modifying enzyme; and optionally simultaneously or sequentially in any order treating said particulate cereal bran fraction with one or more further enzyme.

In a further aspect the present invention relates to a method for increasing the water holding capacity (WHC) of a cereal bran fraction, said method comprising the steps of:

a) Addition of water to a particulate cereal bran fraction to obtain a water content lower than 100% (w/w);
b) Treating said particulate cereal bran fraction with added water without the removal of any components with: one or more cell-wall modifying enzyme; and optionally simultaneously or sequentially in any order treating said particulate cereal bran fraction with one or more further enzyme;
c) Treating said particulate cereal bran fraction from step b) in a heat treatment for a period of time to inactivate further enzyme activity and/or to gelatinization any residual starch, and/or to increase the WHC further, and/or to make the cereal bran stable towards microbial growth.

In a further aspect the present invention relates to a cereal bran fraction with increased WHC produced by a method comprising the steps of:

a) Addition of water to a particulate cereal bran fraction to obtain a water content lower than 100% (w/w);
b) Treating said particulate cereal bran fraction with added water without the removal of any components with: one or more cell-wall modifying enzyme; and optionally simultaneously or sequentially in any order treating said particulate cereal bran fraction with one or more further enzyme;
c) Treating said particulate cereal bran fraction from step b) in a heat treatment for a period of time to inactivate further enzyme activity and/or to gelatinization any residual starch, and/or to increase the WHC further, and/or to make the cereal bran stable towards microbial growth.

It is to be understood that the period of time of a heat treatment under step c) may be varied and optimized depending on temperature applied as well as the requested or wanted residual water content in the bran fraction. In some embodiments, the heat treatment is performed to obtain residual water content of about 10-40%, such as about 5-30% water.

In a further aspect the present Invention relates to the use of a cereal bran fraction with increased WHC produced by the methods according to the present invention for the production of a foodstuff product.

In a further aspect the present invention relates to a foodstuff product obtained by the use of a cereal bran fraction with increased WHC produced by the methods according to the present Invention for the production of a foodstuff product.

In a further aspect the present invention relates to the use of a cell-wall modifying enzyme for increasing the water holding capacity (WHC) of a cereal bran fraction. In some embodiments, the cell-wall modifying enzyme is as defined herein. In some embodiments, the cell-wall modifying enzyme is used in a method as defined herein.

In a further aspect the present invention relates to a kit of parts comprising
a) one or more cell-wall modifying enzyme; and optionally one or more further enzyme;
b) instructions for use in a method according to the present invention; and
c) Optionally other Ingredients for a foodstuff product.

In a further aspect the present invention relates to a cereal bran fraction with a WHC higher than 145% (w/w).

DETAILED DISCLOSURE OF THE INVENTION

An alternative and more natural water-binder than Fibrex would be a cereal bran from e.g. wheat, rye, oat, barley or corn. However, these cereal bi-streams do not have the same water-binding property as Fibrex. By using the method according to the present invention, the water binding properties of cereal bi-streams can be significantly and importantly improved. Utilising this method according to the present invention, millers may be able to upgrade their side-streams from the production of flour, into a product that could compete with products like "Fibrex", however at a lower Cost-In-Use.

Furthermore, the process may further change the solubility of the cereal fibre, making it more soluble, a feature that will both influence the technical nature of the product and the health and nutritional properties. An increased solubility will improve the technical properties, if utilised in many food applications i.e. bread making and breakfast cereals. In both cases a higher degree of solubility will decrease the detrimental effects of adding the bran in regard to processability, appearance and sensoric properties. Increased solubility of the modified bran will enhance the health and nutritional value of the modified bran.

The inventors of the present invention have developed a process that will increase the water-binding of bran side-streams.

Important aspects of the present invention includes the use of a combination of cell wall modifying enzymes, use of low moisture enzymatic treatments of the cereal bran fractions to prevent a too extensive depolymerisation of already soluble cell wall polysaccharides.

Enzymatic treatments may be combined with a heat treatment. The heat treatment may serve as an inactivation step of the enzymes used, however, it may also provide a gelatinization of the residual starch in the raw material, further increasing the water-binding properties of the cereal bran fraction.

The process according to the present invention is intended to "loosen" the structure of the cell wall, gelatinize the residual starch, increasing the water-binding of the cereal bran.

The process is believed to have a high commercial relevance as it may enable millers to upgrade the technological use of the side-streams. These are often used for feed today, but would be upgraded considerably. There has been a long felt need in the art for increasing the water-binding properties of cereal bran.

This modification of the bran, means an upgrading from cattle feed to food grade products. The process will enable bread producers using sugar beet pulp (Fibrex) today, to be able to make a "natural" product. The process of modifying the bran at low water content is a huge advantage, because it can be done by millers who are not use to and who do not have facilities for wet processes. Huge savings can be obtained using the process according to the invention compared to a wet process when the product should be dried to make it stable. The process will upgrade the Health and Nutrition properties of the bran—since the modification will make the bran more soluble.

The process according to the invention may be performed by the use of xylanase, which is expected to be most efficient. However, other cell wall modifying enzymes such as cellulases, glucanases, acetyl xylan esterases, ferulic acid esterases, pectinases and mannanases may have same effect if dosed correctly.

The modification of cereal bran at low water contents, compared to modification at higher water content, will have a huge effect in regard to energy savings, since the evaporation of water/drying will be much less.

The process will be easily handled by millers who normally do not have the equipment to handle liquid processes.

Eventually, set to parameters generating a stable product (in regard to moisture and hence microbial contamination), and a product without residual enzyme activity (eventually to an enzyme activity that will not have a detrimental effect on the following use in application).

The pH during the enzyme treatments should be adjusted to the appropriate pH according to the enzymes used.

Drying processes, the duration, type and temperature of the drying process are well known to the person skilled in the art.

In some embodiments the cereal bran fraction is a side-stream, or by-products of industrial processes. In some embodiments the cereal bran fraction may also contain non-plant material such as a by-product from a fermentation, that may contain yeast and/or bacterial cells.

In some particular embodiments the cereal bran fraction is substantially free of starch or has a reduced content of starch, such as below 40%, such as below 35%, such as below 30%, such as below 25%, such as below 20%, such as below 15%, such as below 10%, such as below 5% (w/w).

In some particular embodiments the cereal bran fraction is from traditional milling, such as wheat bran from traditional milling.

As used herein the term "increasing the water holding capacity (WHC) of a cereal bran fraction" refers to any increase in water holding capacity as compared to the same untreated cereal bran. In some embodiments the term refers to an increase in water holding capacity as compared to the same cereal bran, but without any exogenous enzyme treatment.

As used herein the term "water" refers to any form of water or composition containing water. In some preferred embodiments "water" simply refers to essentially pure water or an aqueous solution with water as the main component.

The term "cereal" as used herein refers to the fruits from a plant of the family Poaceae, such seed containing at least the bran comprising the aleurone, and the starchy endosperm, with or without the additional presence of pericarp, seed coat (alternatively called testa) and/or germ. The term including but not limited to species such as wheat, barley, oat, spelt, rye, sorghum, maize (corn), rice, millet, quinoa, buckwheat, triticale, and fonio.

The terms "bran" as used herein refers to a cereal-derived milling fraction enriched in any or all of the tissues to be selected from aleurone, pericarp and seed coat, as compared to the corresponding intact seed.

The term "milling fraction", as used herein, refers to all or part of the fractions resulting from mechanical reduction of the size of grains, through, as examples but not limited to, cutting, rolling, crushing, breakage or milling, with or without fractionation, through, as examples but not limited to, sieving, screening, sifting, blowing, aspirating, centrifugal sifting, windsifting, electrostatic separation, or electric field separation.

Accordingly, the term "cereal bran fraction" as used herein refers to the cereal fraction obtained directly from the milling that contains the bran. It is to be understood that the cereal bran fraction used in the processes of the present invention has not been subjected to chemical or enzymatic modifications or treatments, such as for the removal of residual starch from the "cereal bran fraction" with subsequent separation or fractionation into fractions high in cereal bran components, such as in aleurone, pericarp and/or seed coat. Thus, a "particulate cereal bran fraction" according to the present invention is not intended to comprise compositions comprising bran that has been treated and/or modified by any exogenous enzyme with subsequent separation or fractionation into a fraction with higher content of bran components, prior to the treatment with one or more cell-wall modifying enzyme, such as by the treatment with any exogenous amylase. Also, a "particulate cereal bran fraction" according to the present invention is not intended to comprise compositions comprising bran that has been subjected to a method step for the removal of starch prior to the treatment with one or more cell-wall modifying enzyme, such as a treatment by ethanol precipitation.

In some embodiments the particulate cereal bran fraction according to the invention contains significant levels of starch, such as more than 2, 4, 6, 8, 10, 12, 14, 16, 18, or 20% w/w prior to the treatment with one or more cell-wall modifying enzyme.

In the context of the present invention, "cell-wall modifying enzyme", refers to any enzyme capable of hydrolysing or modifying the complex matrix polysaccharides of the plant cell wall, such as any enzyme that will have activity in the "cell wall solubilisation assay" included herein. Included within this definition of "cell-wall modifying enzyme" are cellulases, such as cellobiohydrolase I and cellobiohydrolase II, endo-glucanases and beta-glucosidases, and hemicellulolytic enzymes, such as xylanases.

The terms "cellulases" or "cellulolytic enzymes" as used herein are understood as comprising the cellobiohydrolases (EC 3.2.1.91), e.g., cellobiohydrolase I and cellobiohydrolase II, as well as the endo-glucanases (EC 3.2.1.4) and beta-glucosidases (EC 3.2.1.21).

Included with the definition of cellulases are: endoglucanases (EC 3.2.1.4) that cut the cellulose chains at random; cellobiohydrolases (EC 3.2.1.91) which cleave cellobiosyl units from the cellulose chain ends and beta-glucosidases (EC 3.2.1.21) that convert cellobiose and soluble cellodextrins into glucose. Among these three categories of enzymes involved in the biodegradation of cellulose, cellobiohydrolases are the key enzymes for the degradation of native crystalline cellulose. The term "cellobiohydrolase I" is defined herein as a cellulose 1,4-beta-cellobiosidase (also referred to as exo-glucanase, exo-cellobiohydrolase or 1,4-beta-cellobiohydrolase) activity, as defined in the enzyme class EC 3.2.1.91, which catalyzes the hydrolysis of 1,4-beta-D-glucosidic linkages in cellulose and cellotetraose, by the release of cellobiose from the non-reducing ends of the chains. The definition of the term "cellobiohydrolase II activity" is identical, except that cellobiohydrolase II attacks from the reducing ends of the chains.

The cellulases may comprise a carbohydrate-binding module (CBM) which enhances the binding of the enzyme to a cellulose-containing fiber and increases the efficacy of the catalytic active part of the enzyme. A CBM is defined as contiguous amino acid sequence within a carbohydrate-active enzyme with a discreet fold having carbohydrate-binding activity. For further information of CBMs see the CAZy Internet server (Supra) or Tomme et al. (1995) in Enzymatic Degradation of Insoluble Polysaccharides (Saddler and Penner, eds.), Cellulose-binding domains: classification and properties, pp. 142-163, American Chemical Society, Washington. In a preferred embodiment the cellulases or cellulolytic enzymes may be a cellulolytic preparation as defined in U.S. application No. 60/941,251, which is hereby incorporated by reference. In a preferred embodiment the cellulolytic preparation comprising a polypeptide having cellulolytic enhancing activity (GH61A), preferably the one disclosed in WO2005/074656. The cell-wall modifying enzyme may further be a beta-glucosidase, such as a beta-glucosidase derived from a strain of the genus *Trichoderma*, *Aspergillus* or *Penicillium*, including the fusion protein having beta-glucosidase activity disclosed in U.S. application No. 60/832,511 (Novozymes). In some embodiments the cell-wall modifying enzyme is a CBH II, such as *Thielavia terrestris* cellobiohydrolase II (CEL6A). In some embodiments the cell-wall modifying enzyme is a cellulase enzyme, such as one derived from *Trichoderma reesei*.

The cellulolytic activity may, in some embodiments, be derived from a fungal source, such as a strain of the genus *Trichoderma*, such as a strain of *Trichoderma reesei*; or a strain of the genus *Humicola*, such as a strain of *Humicola insolens*.

In some embodiments the cell-wall modifying enzyme is a polypeptide having cellulolytic enhancing activity (GH61A) disclosed in WO 2005/074656; a cellobiohydrolase, such as *Thielavia terrestris* cellobiohydrolase II (CEL6A), a beta-glucosidase (e.g., the fusion protein disclosed in U.S. application No. 60/832,511) and cellulolytic enzymes, e.g., derived from *Trichoderma reesei*.

In some embodiments the cell-wall modifying enzyme is a polypeptide having cellulolytic enhancing activity (GH61A) disclosed in WO 2005/074656; a beta-glucosidase (e.g., the fusion protein disclosed in U.S. application No. 60/832,511) and cellulolytic enzymes, e.g., derived from *Trichoderma reesei*. In some embodiments the cell-wall modifying enzyme is a commercially available product, such as GC220 available from Genencor, A Danisco Division, US or CELLUCLAST® 1.5 L or CELLUZYME™ available from Novozymes A/S, Denmark.

Endoglucanases (EC No. 3.2.1.4) catalyses endo hydrolysis of 1,4-beta-D-glycosidic linkages in cellulose, cellulose derivatives (such as carboxy methyl cellulose and hydroxy ethyl cellulose), lichenin, beta-1,4 bonds in mixed beta-1,3 glucans such as cereal beta-D-glucans or xyloglucans and other plant material containing cellulosic parts. The authorized name is endo-1,4-beta-D-glucan 4-glucano hydrolase, but the abbreviated term endoglucanase is used in the present specification. Endoglucanase activity may be determined using carboxymethyl cellulose (CMC) hydrolysis according to the procedure of Ghose, 1987, Pure and Appl. Chem. 59: 257-268.

In some embodiments endoglucanases may be derived from a strain of the genus *Trichoderma*, such as a strain of *Trichoderma reesei*; a strain of the genus *Humicola*, such as a strain of *Humicola insolens*; or a strain of *Chrysosporium*, preferably a strain of *Chrysosporium lucknowense*.

The term "cellobiohydrolase" means a 1,4-beta-D-glucan cellobiohydrolase (E.C. 3.2.1.91), which catalyzes the hydrolysis of 1,4-beta-D-glucosidic linkages in cellulose, cellooligosaccharides, or any beta-1,4-linked glucose containing polymer, releasing cellobiose from the reducing or non-reducing ends of the chain.

Examples of cellobiohydroloses are mentioned above including CBH I and CBH II from *Trichoderma reseei*; *Humicola insolens* and CBH II from *Thielavia tenrestris* cellobiohydrolase (CELL6A).

Cellobiohydrolase activity may be determined according to the procedures described by Lever et al., 1972, Anal. Biochem. 47: 273-279 and by van Tilbeurgh et al., 1982, FEBS Letters 149: 152-156; van Tilbeurgh and Claeyssens, 1985, FEBS Letters 187: 283-288. The Lever et al. method is suitable for assessing hydrolysis of cellulose in corn stover and the method of van Tilbeurgh et al., is suitable for determining the cellobiohydrolase activity on a fluorescent disaccharide derivative.

The term "beta-glucosidase" means a beta-D-glucoside glucohydrolase (E.C. 3.2.1.21), which catalyzes the hydrolysis of terminal non-reducing beta-D-glucose residues with the release of beta-D-glucose. For purposes of the present invention, beta-glucosidase activity is determined according to the basic procedure described by Venturi et al., 2002, J. Basic Microbiol. 42: 55-66, except different conditions were employed as described herein. One unit of beta-glucosidase activity is defined as 1.0 µmole of p-nitrophenol produced per minute at 500 C, pH 5 from 4 mM p-nitrophenyl-beta-D-glucopyranoside as substrate in 100 mM sodium citrate, 0.01% TWEEN® 20.

In some embodiments the beta-glucosidase is of fungal origin, such as a strain of the genus *Trichoderma, Aspergillus* or *Penicillium*. In some embodiments the beta-glucosidase is a derived from *Trichoderma reesei*, such as the beta-glucosidase encoded by the bgl1 gene (see EP 562003). In another embodiment the beta-glucosidase is derived from *Aspergillus oryzae* (recombinantly produced in *Aspergillus oryzae* according to WO 02/095014), *Aspergillus fumigatus* (recombinantly produced in *Aspergillus oryzae* according to Example 22 of WO 02/095014) or *Aspergillus niger* (1981, J. Appl. 3: 157-163).

The terms "hemicellulolytic enzymes" or "hemicellulases", as used herein, refers to enzymes that may break down hemicellulose.

Any hemicellulase suitable for use in hydrolyzing hemicellulose, preferably into arabinoxylan oligosaccharides, may be used. Preferred hemicellulases include xylanases, arabinofuranosidases, acetyl xylan esterase, feruloyl esterase, glucuronidases, galactanase, endo-galactanase, mannases, endo or exo arabinases, exo-galactanses, pectinase, xyloglucanase, or mixtures of two or more thereof. An example of hemicellulase suitable for use in the present invention includes Grindamyl Powerbake 930 (available from Danisco A/S, Denmark) or VISCOZYM E™ (available from Novozymes A/S, Denmark). In an embodiment the hemicellulase is a xylanase. In an embodiment the xylanase is of microbial origin, such as of fungal origin (e.g., *Trichoderma, Meripilus, Humicola, Aspergillus, Fusarium*) or from a bacterium (e.g., *Bacillus*). In some embodiments the xylanase is derived from a filamentous fungus, preferably derived from a strain of *Aspergillus*, such as *Aspergillus aculeatus*; or a strain of *Humicola*, preferably *Humicola lanuginosa*. The xylanase may preferably be an endo-1,4-beta-xylanase, more preferably an endo-1,4-beta-xylanase of GH 10 or GH11. Examples of commercial xylanases include Grindamyl H121 or Grindamyl Powerbake 930 from Danisco A/S, Denmark or SHEARZYME™ and BIOFEED WHEAT™ from Novozymes A/S, Denmark.

Arabinofuranosidase (EC 3.2.1.55) catalyzes the hydrolysis of terminal non-reducing alpha-L-arabinofuranoside residues in alpha-L-arabinosides. Galactanase (EC 3.2.1.89), arabinogalactan endo-1,4-beta-galactosidase, catalyses the endohydrolysis of 1,4-D-galactosidic linkages in arabinogalactans.

Pectinase (EC 3.2.1.15) catalyzes the hydrolysis of 1,4-alpha-D-galactosiduronic linkages in pectate and other galacturonans.

Xyloglucanase catalyzes the hydrolysis of xyloglucan.

The term "xylanase" as used herein refers to an enzyme that is able to hydrolyze the beta-1,4 glycosyl bond in non-terminal beta-D-xylopyranosyl-1,4-beta-D-xylopyranosyl units of xylan or arabinoxylan. Other names include 1,4-beta-D-xylan xylanohydrolase, 1,4-beta-xylan xylanohydrolase, beta-1,4-xylan xylanohydrolase, (1-4)-beta-xylan 4-xylanohydrolase, endo-1,4-beta-xylanase, endo-(1-4)-beta-xylanase, endo-beta-1,4-xylanase, endo-1,4-beta-D-xylanase, endo-1,4-xylanase, xylanase, beta-1,4-xylanase, beta-xylanase, beta-D-xylanase. Xylanases can be derived from a variety of organisms, including plant, fungal (e.g. species of *Aspergillus, Penicillium, Disporotrichum, Neurospora, Fusarium, Humicola, Trichoderma*) or bacterial species (e.g. species of *Bacillus, Aeromonas, Streptomyces, Nocardiopsis, Thermomyces*) (see for example WO92/17573, WO92/01793, WO91/19782, WO94/21785).

In one aspect of the invention, the xylanase used in the methods of the invention is an enzyme classified as EC 3.2.1.8. The official name is endo-1,4-beta-xylanase. The systematic name is 1,4-beta-D-xylan xylanohydrolase. Other names may be used, such as endo-(1-4)-beta-xylanase; (1-4)-beta-xylan 4-xylanohydrolase; endo-1,4-xylanase; xylanase; beta-1,4-xylanase; endo-1,4-xylanase; endo-beta-1,4-xylanase; endo-1,4-beta-D-xylanase; 1,4-beta-xylan xylanohydrolase; beta-xylanase; beta-1,4-xylan xylanohydrolase; endo-1,4-beta-xylanase; beta-D-xylanase.

The reaction catalyzed Is the endohydrolysis of 1,4-beta-D-xylosidic linkages in xylans.

In one aspect of the invention, the xylanase of the invention is a xylanase of Glycoside Hydrolase (GH) Family 11. The term "of Glycoside Hydrolase (GH) Family 11" means that the xylanase in question is or can be classified in the GH family 11.

In one aspect of the invention, the xylanase used according to the invention, is a xylanase having xylanase activity as measured in the "Xylanase assay" as described herein.

According to the Cazy(ModO) site, Family 11 glycoside hydrolases can be characterised as follows:
Known Activities: xylanase (EC 3.2.1.8)
Mechanism: Retaining
Catalytic Nucleophile/Base: Glu (experimental)
Catalytic Proton Donor: Glu (experimental)
3D Structure Status: Fold: β-jelly roll
Clan: GH-C As used herein, "Clan C" or "Clan" refers to groupings of families which share a common three-dimensional fold and identical catalytic machinery (see, for example, Henrissat, B. and Bairoch, A., (1996) Biochem. J., 316, 695-696).

As used herein, "Family 11" refers to a family of enzymes as established by Henrissat and Bairoch (1993) Biochem J., 293, 781-788 (see, also, Henrissat and Davies (1997) Current Opinion in Structural Biol. 1997, &: 637-644). Common features for family 11 members include high genetic homology, a size of about 20 kDa and a double displacement catalytic mechanism (see Tenkanen et al., 1992; Wakarchuk et al., 1994). The structure of the family 11 xylanases includes two large β-sheets made of β-strands and α-helices.

Family 11 xylanases include the following: *Aspergillus niger* XynA, *Aspergillus kawachii* XynC, *Aspergillus tubigensis* XynA, *Bacillus circulans* XynA, *Bacillus punzilus* XynA, *Bacillus subtilis* XynA, *Neocalliniastix patriciarum* XynA, *Streptomyces lividans* XynB, *Streptomyces lividans* XynC, *Streptomyces therinoviolaceus* XynII, *Thermomonospora fusca* XynA, *Trichoderma harzianum* Xyn, *Trichoderma reesei* XynI, *Trichoderma reesei* XynII, *Trichodermaviride Xyn*.

It is to be understood that the enzymes used according to the present invention are preferably exogenous to the cereal bran used, i.e. not originating from the cereal bran used.

Enzyme activity assays according to the invention:
Cell Wall Solubilisation Assay:
Bran solubility may be measured using the following assay.

A suspension of wheat bran in (0.1 M)-di-sodium-hydrogen phosphate (0.2 M) buffer, pH 5.0 is prepared to an concentration of 1.33% bran (w/w). From this suspension, aliquots of 750 µl are transferred into Eppendorf tubes under stirring. Each substrate tube is pre-heated for 5 minutes at 40° C. Hereto, 250 µl enzyme solution is added, making the end concentration of substrate 1%. Three dilutions (in duplicate) are made from each enzyme composition according to the invention, with increasing enzyme concentration (e.g. 0.33; 1.0 and 3.0 µg enzyme/gram bran) to each time of determination (0, 30, 60 and 240 minutes). As blank, a heat denaturated solution of the enzyme composition is used. The reaction is terminated to the given times, by transferring the tubes to a incubator set at 95° C. Heat denaturated samples are kept at 4° C. until all enzyme reactions are terminated. When all enzyme reactions are terminated, Eppendorph tubes are centrifuged to obtain a clear supernatant. The enzymes capability to solubilise bran is expressed as the increase in reducing end groups as determined using PAH-BAH (Lever, 1972).

If the bran used contain residual starch, side activities such as amylase activity, may interfere with the above assay, bran solubilisation assay should only be carried out on purified cell wall modifying enzymes (having no amylase activity).

Xylanase Assay (Endo-β-1,4-Xylanase Activity)

Samples were diluted in citric acid (0.1 M)-di-sodium-hydrogen phosphate (0.2 M) buffer, pH 5.0, to obtain approx. $OD_{590}$=0.7 in this assay. Three different dilutions of the sample were pre-incubated for 5 minutes at 40° C. At time=5 minutes, 1 Xylazyme tablet (crosslinked, dyed xylan substrate, Megazyme, Bray, Ireland) was added to the enzyme solution in a reaction volume of 1 ml. At time=15 minutes the reaction was terminated by adding 10 ml of 2% TRIS/NaOH, pH 12. Blanks were prepared using 1000 µl buffer instead of enzyme solution. The reaction mixture was centrifuged (1500×g, 10 minutes, 20° C.) and the OD of the supernatant was measured at 590 nm. One xylanase unit (XU) is defined as the xylanase activity increasing $OD_{590}$ with 0.025 per minute.

In some aspects the present invention provides a cereal bran fraction prepared according to the present invention that may be used as a foodstuff, or as a foodstuff ingredient.

Suitably, the term "foodstuff" as used herein may mean a foodstuff in a form which is ready for consumption. Alternatively or in addition, however, the term foodstuff as used herein may mean one or more food materials which are used in the preparation of a foodstuff. By way of example only, the term foodstuff encompasses both baked goods produced from dough as well as the dough used in the preparation of said baked goods.

Suitably, the term "foodstuff" as used herein means a substance which is suitable for human and/or animal consumption.

In another aspect, the foodstuff in accordance with the present invention may be an animal feed. In some embodiment the foodstuff is a petfood, such as a dog or cat food.

In some embodiments, the foodstuff used according to the present invention is selected from one or more of the following: eggs, egg-based products, including but not limited to mayonnaise, salad dressings, sauces, ice creams, egg powder, modified egg yolk and products made therefrom; baked goods, including breads, cakes, sweet dough products, laminated doughs, liquid batters, muffins, doughnuts, biscuits, crackers and cookies; confectionery, including chocolate, candies, caramels, halawa, gums, including sugar free and sugar sweetened gums, bubble gum, soft bubble gum, chewing gum and puddings; frozen products including sorbets, preferably frozen dairy products, including ice cream and ice milk; dairy products, including cheese, butter, milk, coffee cream, whipped cream, custard cream, milk drinks and yoghurts; mousses, whipped vegetable creams, meat products, including processed meat products; edible oils and fats, aerated and non-aerated whipped products, oil-in-water emulsions, water-in-oil emulsions, margarine, shortening and spreads including low fat and very low fat spreads; dressings, mayonnaise, dips, cream based sauces, cream based soups, beverages, spice emulsions and sauces.

Suitably the foodstuff in accordance with the present invention may be a "fine foods", including cakes, pastry, confectionery, chocolates, fudge and the like.

In one aspect the foodstuff in accordance with the present invention may be a dough product or a baked product, such as a bread, a fried product, a snack, cakes, pies, brownies, cookies, noodles, instant noodles, tortillas, snack items such as crackers, graham crackers, pretzels, and potato chips, and pasta, and breakfast cereals.

In a further aspect, the foodstuff in accordance with the present invention may be a plant derived food product such as flours, pre-mixes, oils, fats, cocoa butter, coffee whitener, salad dressings, margarine, spreads, peanut butter, shortenings, ice cream, cooking oils.

In another aspect, the foodstuff in accordance with the present invention may be a dairy product, including butter, milk, cream, cheese such as natural, processed, and imitation cheeses in a variety of forms (including shredded, block, slices or grated), cream cheese, ice cream, frozen desserts, yoghurt, yoghurt drinks, butter fat, anhydrous milk fat, other dairy products. The enzyme used according to the present invention may improve fat stability in dairy products.

In another aspect, the foodstuff in accordance with the present invention may be a food product containing animal derived ingredients, such as processed meat products, cooking oils, shortenings.

In a further aspect, the foodstuff in accordance with the present invention may be a beverage, a fruit, mixed fruit, a vegetable or wine.

In another aspect, the foodstuff in accordance with the present invention may be an animal feed. Suitably, the animal feed may be a poultry feed. When the foodstuff is poultry feed, the present invention may be used to lower the cholesterol content of eggs produced by poultry feed on the foodstuff according to the present invention.

In one aspect preferably the foodstuff is selected from one or more of the following: eggs, egg-based products, including mayonnaise, salad dressings, sauces, ice cream, egg powder, modified egg yolk and products made there from.

Preferably the foodstuff according to the present invention is a water containing foodstuff. Suitably the foodstuff may be comprised of 10-98% water, suitably 14-98%, suitably of 18-98% water, suitably of 20-98%, suitably of 40-98%, suitably of 50-98%, suitably of 70-98%, suitably of 75-98%.

The cereal bran fraction with increased WHC may be used as a food improver.

In one aspect of the invention the food improver is a cake improver.

In one aspect of the invention the food improver is a bread improver.

The food improver generated according to the present invention may suitably comprise one or more of the following additives:
soy protein material; carotenoids, flavenoids, antioxidant and phytochemical (especially anthocyanonide, carotenoid, bioflavinoid, glutathione, catechin, isoflavone, lycopene, ginsenoside, pycnogenol, alkaloid, pygeum phytosterol, suiphoraphone, resveretol, grape seed extract or food containing stanol esters), vitamin (especially vitamin C, vitamin A, vitamin B3, vitamin D, vitamin E, thiamine, riboflavin, niacin, pyridoxine, cyanocobalamin, folic acid, biotin, pantothenic acid or vitamin K), minerals (especially calcium, iodine, magnesium, zinc, iron, selenium, manganese, chromium, copper, cobalt, molybdenum or phosphorus), fatty acid (especially gamma-linoleic acid, ucospentaenoic acid or decosahexaenoic acid), oil (especially borage oil, high carotenoid canola oil or flax seed oil), glucerol, sorbitol, amino acid (especially tryptophan, lysine, methionine, phenylalanine, threonine, valine, leucine, isoleucine, alanine, arginine, aspartic acid, cystine, cysteine, glutamic acid, glutamine, glycine, histidine, proline, hydroxyproline, serine, taurine or tyrosine), enzyme as defined above (especially bromelaln, papain, amylase, cellulase or coenzyme Q), lignin, stanol ester or friendly bacteria (especially *Lactobacillus acidophilus, Lactobacillus bulgaricus, Lactobacillus bifidus, Lactobacillus plantarum* or *Streptococcus faecium*), folic acid, insoluble and/or soluble fibre.

The present invention may provide one or more of the following unexpected technical effects in egg products, particularly mayonnaise: improved heat stability during pasteurisation; improved organoleptic properties, an improved consistency.

The present invention may provide one or more of the following unexpected technical effects in dough and/or baked products: an improved specific volume of either the dough or the baked products (for example of bread and/or of cake); an improved dough stability; an improved crust score (for example a thinner and/or crispier bread crust), an improved crumb score (for example a more homogenous crumb distribution and/or a finer crumb structure and/or a softer crumb); an improved appearance (for example a smooth surface without blisters or holes or substantially without blisters or holes); a reduced staling; an enhanced softness; an improved odour; an improved taste.

These functional compounds, such as a cereal bran fraction treated by the methods according to the present invention may then be used in the manufacture of a dough and/or a baked product, comprising adding said functional compounds to a dough, and (optionally) baking the dough to make a baked product for one or more of the following: reducing stickiness of the dough; improving machinability of the dough; reducing blistering during baking of the baked product; improving bread volume and/or softness; prolonging shelf life of the baked product and/or dough; improving antistaling effect of the baked product and/or dough; improving crumb structure of the baked product; reducing pore heterogeneity of the baked product; improving pore homogeneity of the baked product; reducing mean pore size of the baked product; enhancing the gluten index of the dough; improving flavour and/or odour of the baked product, improving the colour of the crust of the baked product.

In one aspect the functional compounds generated by the methods according to the present invention are purified or partly purified.

In one aspect the functional compounds generated by the methods according to the present invention are not further purified before use in a foodstuff.

In one aspect the functional compounds generated by the methods according to the present invention are formulated into a dry product.

In one aspect the functional compounds are concentrated or diluted before use in a foodstuff.

In another aspect of the invention, there is provided a method of making noodles, or a noodle dough or a noodle-based product, which method comprises adding a functional compound according to the present invention to the noodle, noodle dough or noodle-based product.

In one aspect of the present invention, there is provided a use of a functional compound according to the present invention in the manufacture of a noodle or a noodle-based product for one or more of improving colour/yellowness, stabilising colour characteristics, reducing brightness, reducing fat content, improving texture and bite (chewiness), reducing water activity, reducing breakage, increasing core firmness and improving shape retention during processing.

In another aspect of the invention, there is provided a method of making a tortilla or tortilla dough, which method comprises adding a food improver generated according to the present invention to the tortilla or tortilla dough.

In another aspect of the invention, there is provided a method of making pasta or whole grain pasta or a pasta dough, which method comprises adding a food improver generated according to the present invention to the pasta or pasta dough.

A further aspect of the present invention provides the use of a food improver generated according to the present invention in the manufacture of a tortilla or a tortilla dough for improving the ability to role of a tortilla, increasing pliability of a tortilla, improving antistaling properties of the tortilla and/or tortilla dough, improving softness and/or reducing off-flavour in the tortilla and/or tortilla dough.

The functionality of the food improver may be improved by combination with emulsifiers such as DATEM.

Suitably, the present invention may provide one or more of the following unexpected technical effects in a foodstuff: an improved appearance, an improved mouth feel, an improved stability, in particular an improved thermal stability, an improved taste, an improved softness, an improved resilience, an improved emulsification.

Suitably, the present invention may provide one or more of the following unexpected technical effects in dairy products, such as ice cream for example: an improved mouth feel (preferably a more creamy mouth feel); an improved taste; an improved meltdown.

Suitably, the present invention may provide one or more of the following unexpected technical effects in egg or in egg products: improved stability of emulsion; thermal stability of emulsion; improved flavour; reduced mal-odour; improved thickening properties, improved consistency.

Specific technical effects associated with the use of the food improver as defined herein in the preparation of a foodstuff are listed in the table below:

| | Foodstuff | Effect |
|---|---|---|
| 1 | Bread, Muffins and Doughnuts | Strengthens dough and increases mechanical resistance and increases water absorption capacity. Increases volume of bakery products and maintains softness of crumb |
| 2 | Frozen dough | Prevents spoiling during refrigeration |
| 3 | Sponge cake | Makes good cake volume and a uniform soft texture |
| 4 | Biscuit, cracker and cookie | Makes stable emulsions of fat and prevents stickiness to the machine. Prevents blooming of high fat products |
| 5 | Batter and breading | Improves texture of fried products. |
| 6 | Noodles | Prevents dough from sticking to the machine. Increases water content, and decreases cooking loss |
| 7 | Instant noodles | Prevent noodles form adhering to each other |
| 8 | Pasta | Dough conditioner prevents adhesion on cooking. |
| 9 | Custard cream | Makes starch paste with a smooth and creamy texture, and prevents dehydration. |
| 10 | Coffee whitener | Prevent oil and water separation |
| 11 | Whipping cream | Provides stable emulsion |
| 12 | Chocolate | Prevents or reduced blooming |
| 13 | Caramel, candy and nougat | Improves emulsification of molten sugar and oil. Prevents separation of oil. |
| 14 | Processed meat, sausages | Improves water holding capacity of sausages and pressed ham, and prevents separation of oil phase of pastes and pâté. |

The food improver may also be used in bread-improving additive, e.g. dough compositions, dough additive, dough conditioners, pre-mixes and similar preparations conventionally added to the flour and/or the dough during processes for making bread or other baked products to provide improved properties to the bread or other baked products.

Thus, the present invention further relates to a bread-improving composition and/or a dough-improving composition comprising a food improver generated according to the present invention; and also to a dough or baked product comprising such a bread-improving and/or dough-improving composition.

The bread-improving composition and/or dough-improving composition may comprise, in addition to bran fraction obtained according to the present invention, other substances, which substances are conventionally used in baking to improve the properties of dough and/or baked products.

The bread-improving composition and/or dough-improving composition may comprise one or more conventional baking agents, such as one or more of the following constituents:

A milk powder, gluten, an emulsifier, granulated fat, an oxidant, an amino acid, a sugar, a salt, flour or starch.

When functional compounds, generated by the methods according to the present invention, such as a cereal bran fraction treated with one or more enzyme, are used in the manufacture of a dough and/or a baked product gluten may advantageously be added. Gluten may be added to a concentration range of about 0-15% (w/w) of the flour used in the dough, such as in the range of about 6-15%, such as in a range of about 6-10%, such as about 6%.

Examples of suitable emulsifiers are: monoglycerides, diacetyl tartaric acid esters of mono- and diglycerides of fatty acids, sugar esters, sodium stearoyl lactylate (SSL) and lecithins.

The bread and/or dough improving composition may further comprise another enzyme, such as one or more other suitable food grade enzymes, including starch degrading enzymes such as endo- or exoamylases, pullulanases, debranching enzymes, hemicellulases including xylanases, cellulases, oxidoreductases, e.g. glucose oxidase, pyranose oxidase, sulfhydryl oxidase or a carbohydrate oxidase such as one which oxidises maltose, for example hexose oxidase (HOX), lipases, phospholipases, galactolipases, and hexose oxidase, proteases and acyltransferases (such as those described in WO04/064987 for instance).

The term "baked product" as used herein includes a product prepared from dough. Examples of baked products (whether of white, light or dark type) which may be advantageously produced by the present invention include one or more of the following: bread (including white, whole-meal and rye bread), typically in the form of loaves or rolls or toast, French baguette-type bread, pita bread, tortillas, tacos, cakes, pancakes, biscuits, crisp bread, pasta, noodles and the like.

The dough in accordance with the present invention may be a leavened dough or a dough to be subjected to leavening. The dough may be leavened in various ways such as by adding sodium bicarbonate or the like, or by adding a suitable yeast culture such as a culture of *Saccharomyces cerevisiae* (baker's yeast).

The dough in accordance with the present invention may be dough for preparation of a dry cereal product, a crisp bread, a biscuit or a cracker.

SPECIFIC EMBODIMENTS OF THE INVENTION

In some embodiments the one or more cell-wall modifying enzyme used according to the present invention is selected from the group consisting of a hemicellulase, such as a xylanase, ferulic acid esterases, acetyl xylan esterases, and/or a pectinase, and a cellulase, such as cellobiohydrolases, endo-glucanases, a mannanase, and a beta-glucanase.

In some embodiments the cellulase used according to the present invention is selected from an endo-cellulase, an exo-cellulase, a cellobiase, an oxidative cellulases, a cellulose phosphorylases.

In some embodiments the one or more further enzyme used according to the present invention is selected from the group consisting of a hemicellulase, such as a xylanase, ferulic acid esterases, acetyl xylan esterases, and/or a pectinase, and a cellulase, such as cellobiohydrolases, endo-glucanases, a mannanase, a beta-glucanase, a protease, an amylase, an oxidative enzyme or a crosslinking enzyme such as a transglutaminase.

In some embodiments the cereal bran fraction is treated in the methods according to the present invention with only one or more cell-wall modifying enzyme and not any further enzyme.

In some embodiments the cereal bran fraction is treated in the methods according to the present invention with one or more further enzyme after said treatment with one or more cell-wall modifying enzyme.

In some embodiments the cereal bran fraction is not treated in the methods according to the present invention with an amylase.

By "amylase" is meant to include any amylase such as glucoamylases, α-amylase, β-amylases and wild-type α-amylases of *Bacillus* sp., such as *B. licheniformis* and *B. subtilis*. "Amylase" shall mean an enzyme that is, among other things, capable of catalyzing the degradation of starch. Amylases are hydrolases that cleave the α-D-(I→4) O-glycosidic linkages in starch. Generally, α-amylases (EC 3.2.1.1; (X-D-(I→4)-glucan glucanohydrolase) are defined as endo-acting enzymes cleaving α-D-(I→4) O-glycosidic linkages within the starch molecule in a random fashion. In contrast, the exo-acting amylolytic enzymes, such as β-amylases (EC 3.2.1.2; α-D-(I→4)-glucan maltohydrolase) and some product-specific amylases like maltogenic α-amylase (EC 3.2.1.133) cleave the starch molecule from the non-reducing end of the substrate, β-Amylases, α-glucosidases (EC 3.2.1.20; α-D-glucoside glucohydrolase), glucoamylase (EC 3.2.1.3; α-D-(I-→4)-glucan glucohydrolase), and product-specific amylases can produce glucose from starch.

In some embodiments the cereal bran fraction is further treated in a heat treatment for a period of time to inactivate further enzyme activity and/or to gelatinization any residual starch, and/or to increase the WHC further.

In some embodiments the cereal bran fraction is treated in a heat treatment at a temperature in the range of 40-300° C., such in the range of 50-150° C., such as in a range of 60-120° C., such as in the range of 60-90° C.

In some embodiments the cereal bran fraction is treated in a heat treatment step to reduce water content at a temperature, wherein the enzyme activity is not significantly reduced, such as at a temperature in the range of 40-60° C. for a period of time sufficient to reduce water content in the cereal bran fraction to a substantially dry product.

In some embodiments the treated cereal bran fraction has an increased solubility to a degree as determined on drymatter versus drymatter bran higher than 5%, such as higher than 10%, such as higher than 15%, such as higher than 20%, such as higher than 25%, such as higher than 30%, such as higher than 35%, such as in the range of 10%-40%, such as in the range of 15%-40%, such as in the range of 15%-35%, such as in the range of 10%-35%.

In some embodiments the treated cereal bran fraction is solubilised to a degree as determined on drymatter versus drymatter bran higher than 5%, such as higher than 10%, such as higher than 15%, such as higher than 20%, such as higher than 25%, such as higher than 30%, such as higher than 35%, such as in the range of 10%-40%, such as in the range of 15%-40%, such as in the range of 15%-35%, such as in the range of 10%-35%.

The degree of solubility as described by a drymatter versus drymatter percentage is as determined in the bran solubility assay described in the examples.

In some embodiments the average particle size of said particulate bran is below 3000 µm, such as below 1000 µm, such as below 500 µm.

In some embodiments the cereal bran fraction used in the method according to the present invention is obtained from an industrial milling process and further milled to obtain an average particle size below 500 µm, such as below 400 µm, such as below 200 µm.

In some embodiments the cereal bran fraction is selected from wheat, barley, oat, rye and triticale, rice, and corn.

In some embodiments the cereal bran fraction is derived from a cereal side-stream from processing of plant material, such as soap stocks from refining of vegetable oils, brewers spent grain or Destillers dried spent grain with solubles (DDGS).

In some embodiments the method according to the present invention further comprises a step of spray drying the treated cereal bran fraction.

In some embodiments the method according to the present invention further comprises a step of lyophilisation of the treated cereal bran fraction.

In some embodiments the cereal bran fraction is treated according to the present invention to obtain a WHC higher than 150% (w/w), such as higher than 160% (w/w), such as higher than 170% (w/w), such as higher than 180% (w/w), such as higher than 190% (w/w), such as higher than 200% (w/w).

It is to be understood that any specific value of a WHC, or an increase in WHC as mentioned herein, refers to a value of a WHC or Increase in WHC corresponding to the value of a WHC or increase in WHC as determined in the assay "Determination of water holding capacity (WHC)" as described herein.

In some embodiments the cereal bran fraction according to the present invention has a WHC higher than 150% (w/w), such as higher than 160% (w/w), such as higher than 170% (w/w), such as higher than 180% (w/w), such as higher than 190% (w/w), such as higher than 200% (w/w).

In some embodiments the cereal bran fraction is treated according to the present invention under step b) at a temperature in the range 10-70° C., such as in the range of 20-60° C., such in the range of 30-50° C.

In some embodiments the water is added according to the present invention under step a) to obtain a water content in the range of 5-100% (w/w), such as in the range of 10-90% (w/w), such as in the range of 15-80% (w/w), such as in the range of 20-70% (w/w), such as in the range of 30-60% (w/w), such as in the range of 40-50% (w/w), or lower than 90% (w/w), such as lower than 80% (w/w), such as lower than 70% (w/w), such as lower than 60% (w/w), such as lower than 50% (w/w).

It is to be understood that the percentage of "a water content" obtained by the addition of water refers to the weight of added water per weight of bran. Accordingly, when 45 g water is added to 100 g bran, the water content obtained is 45% w/w.

In some embodiments the particulate cereal bran is treated according to the present invention under step b) with one or more cell-wall modifying enzyme in a concentration ranging from 0.01 mg enzyme protein to 2 mg enzyme protein per kg cereal bran fraction, such as in the range of 0.01 mg enzyme protein to 1 mg enzyme protein, such as in the range of 0.01 mg enzyme protein to 0.5 mg enzyme protein.

In some embodiments the particulate cereal bran is treated according to the present invention under step b) with one or more cell-wall modifying enzyme in a period of time in the range from 1-10000 minutes, such as in the range from 5-1440 minutes, such as in the range of 10-240 minutes, such as in the range of 10-120 minutes. In some embodiments the cereal bran fraction with increased WHC obtained in the method according to the present invention is added directly in the production of the foodstuff product.

In some embodiments the foodstuff product according to the present invention is selected from the group consisting of bread, a breakfast cereal, a pasta, biscuits, cookies, snacks, and beer.

All patents, patent applications, and published references cited herein are hereby incorporated by reference in their entirety. The disclosure set forth herein has been particularly shown and described with references to preferred embodiments thereof, it will be understood by those skilled in the art that various changes in form and details may be made therein without departing from the scope encompassed by the present disclosure.

Example 1

Materials:
Bran:

Two cereal bran fractions were used, one from rye and one from wheat (hereafter rye and wheat) having the following composition:

| Sample | Moisture | Protein | Fibre | Ash | Starch |
|---|---|---|---|---|---|
| Rye bran | 8.33 | 14.49 | 7.42 | 4.83 | 22.98 |
| Wheat bran | 8.16 | 15.58 | 8.91 | 6.38 | 21.39 |

As a bench mark, Fibrex 595 is used.

Enzymes:

Grindamyl PowerBake 950 (Xylanase) was used to modify the cereal bran.

Methods:

Bran Modification:

Bran was added water (+/− enzyme) to a water content of 45% w/w (e.g. 45 g water added to 100 g bran), under mixing. The bran added water (+/− enzyme) was left at 40° C. in 30 minutes for modification of the bran constituents. Hereafter the bran was dried in an oven (80° C., over night). The drying process may have three main purposes; 1) the modified bran may be dried to obtain a stable product. 2) the process will gelatinize the residual starch in the bran, increasing the water holding capacity of the modified bran and 3) the process will inactivate the enzymes added.

Determination of Water Holding Capacity (WHC):

5 gram of bran is weighed into a 50 ml centrifugation tube. Tube and sample is weighed (weight_1). Hereafter 25 ml of demineralised water is added and the sample is mixed, by slowly turning over the sample using a rotater (Stuart SB2, Bie & Berntsen, Denmark), at room temperature for 60 minutes. Hereafter the hydrated sample is centrifuged (1700×g, 10 minutes, 20° C.). The supernatant is decanted and the tube with hydrated sample is weighed (weight_2).

WHC in percent can be calculated according to equation 1.

$$\text{WHC, \%} = ((\text{weight\_2} - \text{weight\_1})*100\%)/5 \text{ gram sample.} \quad \text{Equation 1:}$$

Determination of Bran Solubility:

1 gram of bran or modified bran was added 5 mL demineralised water in a sealed tube, and extracted for 30 minutes at ambient via rotation. Hereafter the tube was centrifuged at 1500×g, ambient temperature. The supernatant was recovered and dry matter content in the supernatant was determined using a HB43-S Halogen Moisture analyser (Mettler Toledo).

The dry matter recovery in the supernatant should be corrected for the amount of supernatant vs the amount of extraction liquid volume used.

Results:

Using the bran samples and protocol mentioned above, the results in table 1 and FIG. 1 was obtained.

TABLE 1

WHC (%) of rye and wheat bran as a function of treatment and the standard error calculated based on doublet determinations (std WHC, % - rye and wheat respectively; low, med, and high enzyme refers to a concentration of enzyme protein per kg bran in an amount of 0.05 mg enzyme protein/kg; 0.25 mg enzyme protein/kg, and 1.25 mg enzyme protein/kg).

| Treatment | WHC Rye, % | Std WHC, % Rye | WHC Wheat, % | Std Wheat, % |
|---|---|---|---|---|
| none | 141.1 | 0.71 | 144 | 2.26 |
| process | 177 | 0.85 | 250.8 | 1.13 |
| process, low enz | 189 | 1.41 | 255.7 | 0.42 |
| process, med enz | 188.5 | 0.71 | 251.1 | 5.23 |
| Process, high enz | 181.7 | 2.97 | 236 | 0.57 |

Figure 1:
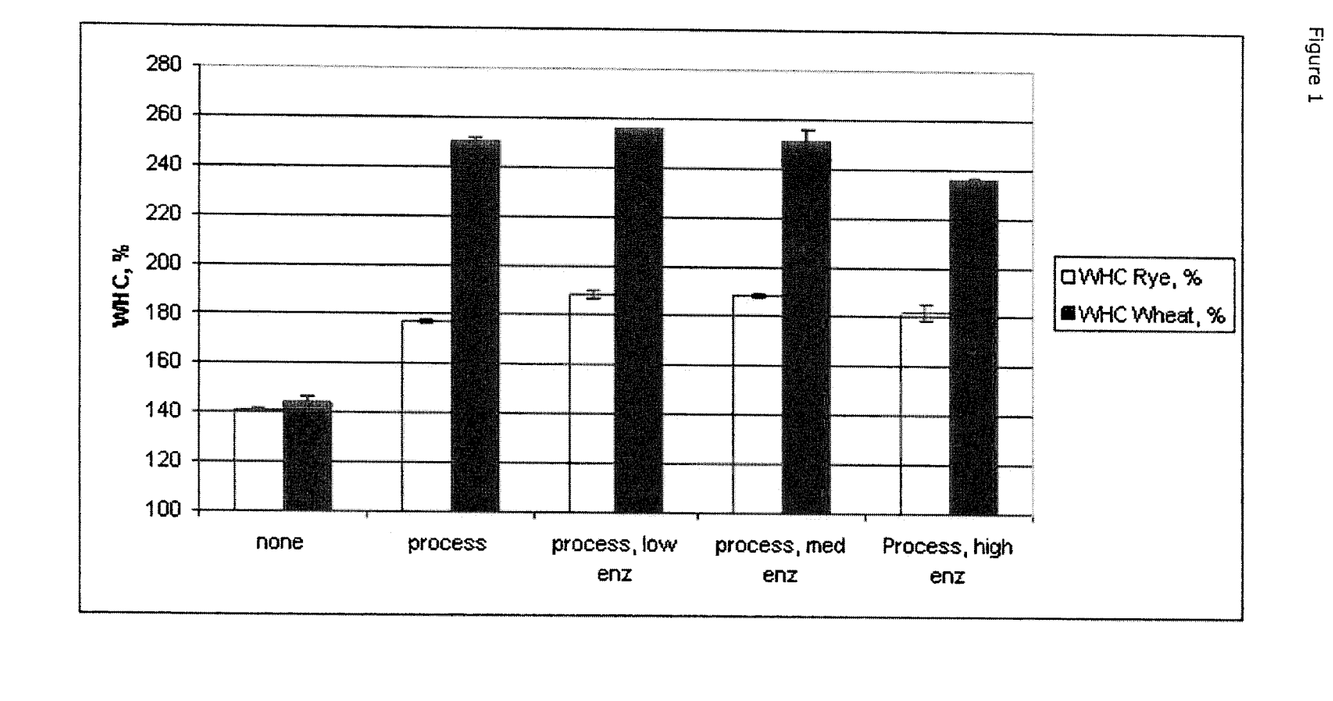
FIG. 1. WHC (%) of rye and wheat bran as a function of treatment. Error bars indicate the standard error calculated from doublet determinations.

The results in table 1 are illustrated in FIG. 1.

As can be seen from the results, the process has a significant effect on the water holding capacity of the bran. To bench mark the effect obtained in this initial trail, the results were compared to the water holding capacity of Fibrex 595. Results are reported in table 2 and FIG. 2.

TABLE 2

WHC (%) of wheat bran as a function of treatment and of Fibrex 595. The standard error is based on doublet determinations (std WHC, % - rye and Fibrex respectively).

| Treatment | WHC Wheat, % | Std Wheat, % | WHC Fibrex 595, % | Std Fibrex 595, % |
|---|---|---|---|---|
| none | 144 | 2.26 | 305 | 0.00 |
| process, low enz | 256 | 0.42 | | |

Figure 2:
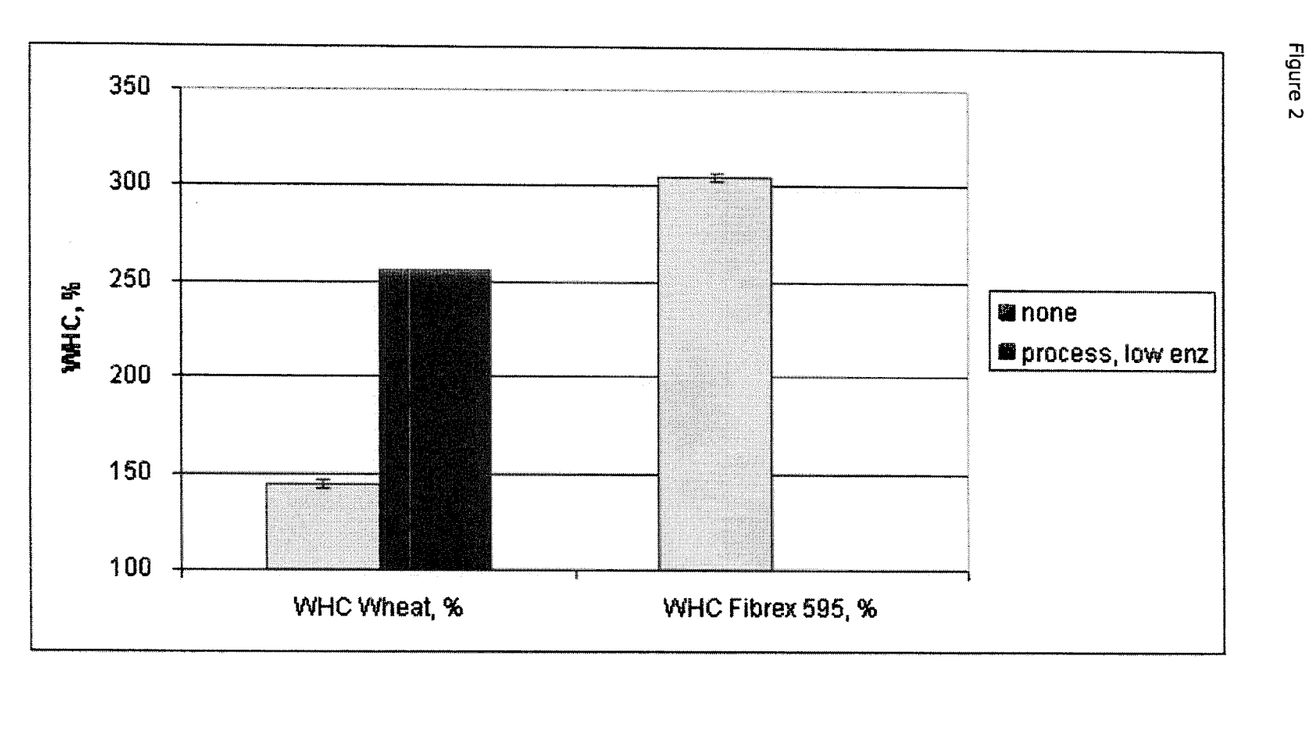
FIG. 2. WHC (%) of wheat bran as a function of treatment and of Fibrex 595. Error bars indicate the standard error calculated from doublet determinations.

The results in table 2 are illustrated in FIG. 2.

Figure 3:
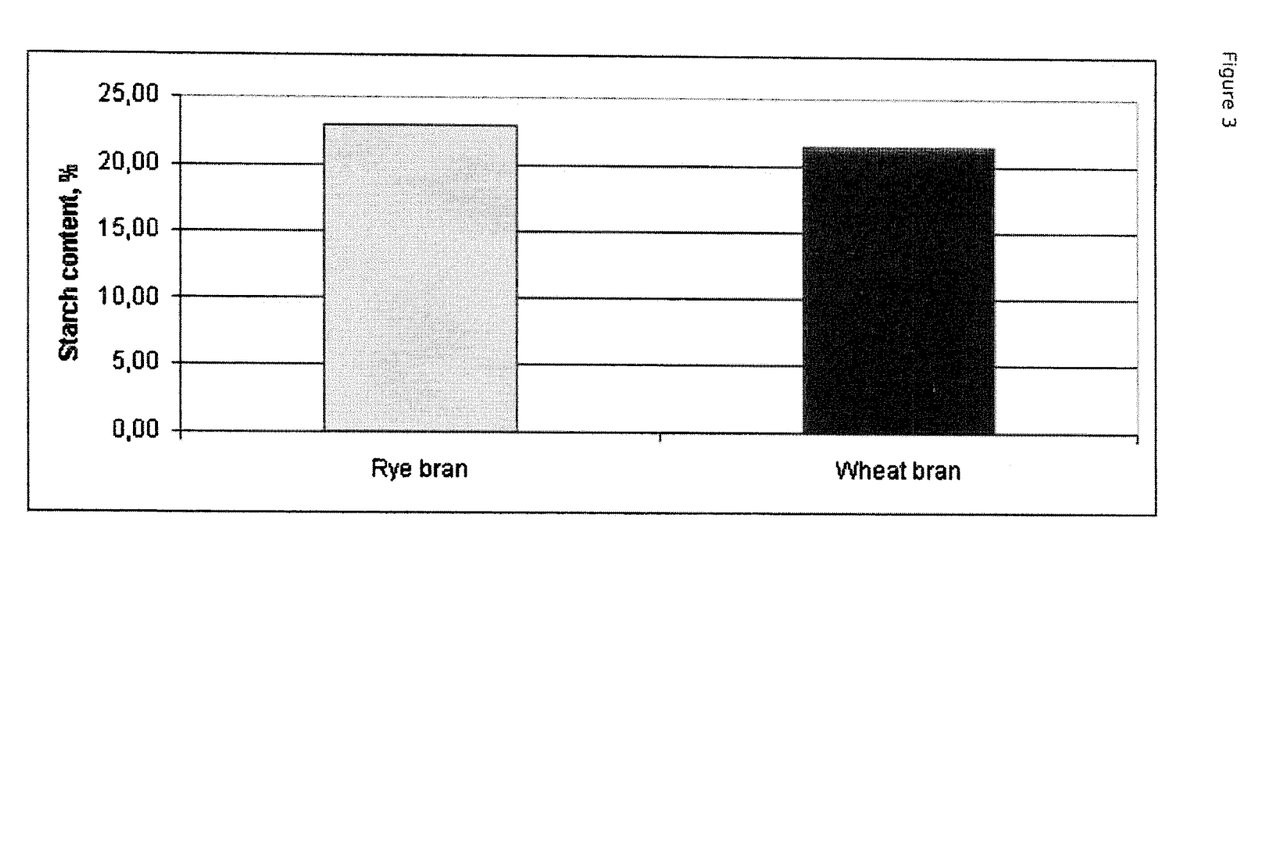
FIG. 3. Starch content (%) in bran samples (Rye (grey) and wheat (black)).

To further investigate whether the difference in water holding capacity between the rye and wheat bran is due to difference in starch content or due to structural differences between the bran cell wall material, the starch content in the two samples was investigated. The results are summarised in FIG. 3.

Figure 4:
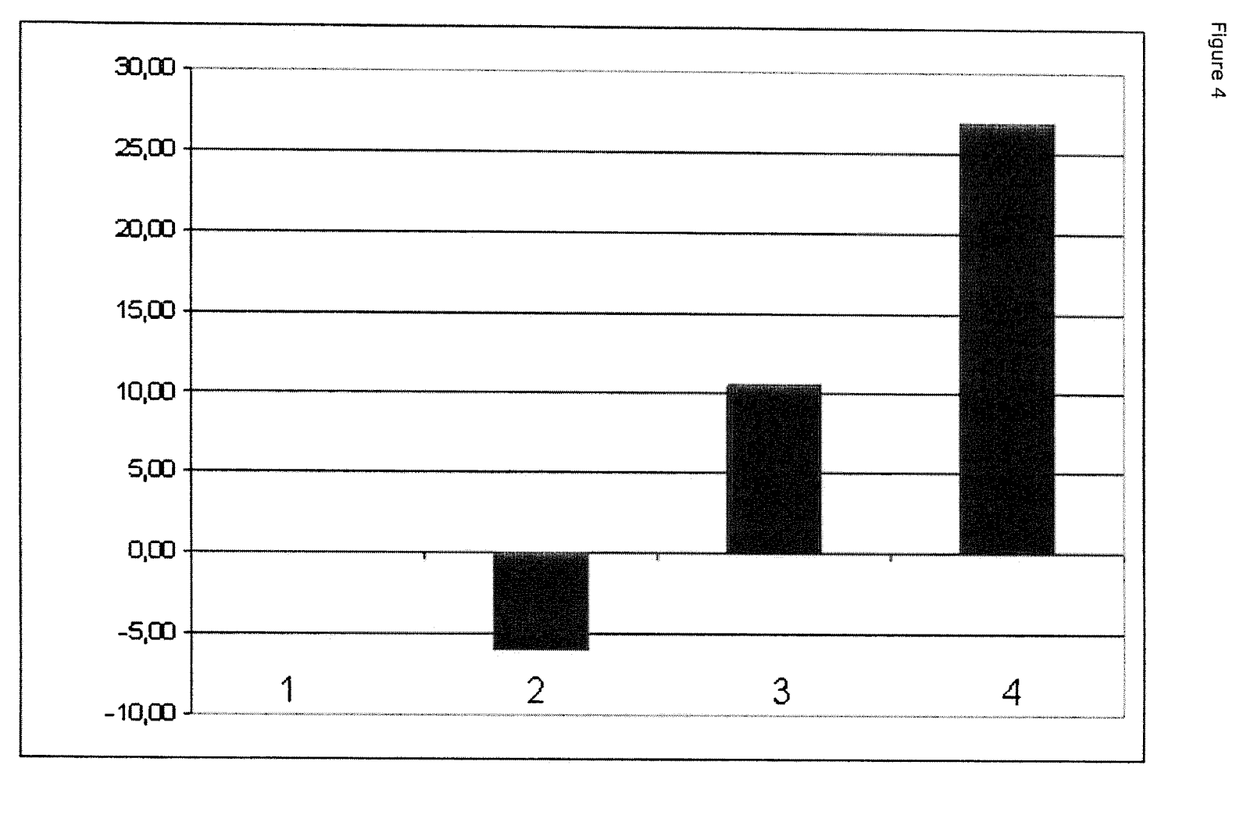
FIG. 4. Relative Bran solubility (%) as a function of bran treatment (1: Untreated wheat bran; 2: Processed wheat bran without enzyme treatment; 3: Processed wheat bran, low xylanase dose; and 4: Processed wheat bran, medium xylanase dose).
Figure 5:
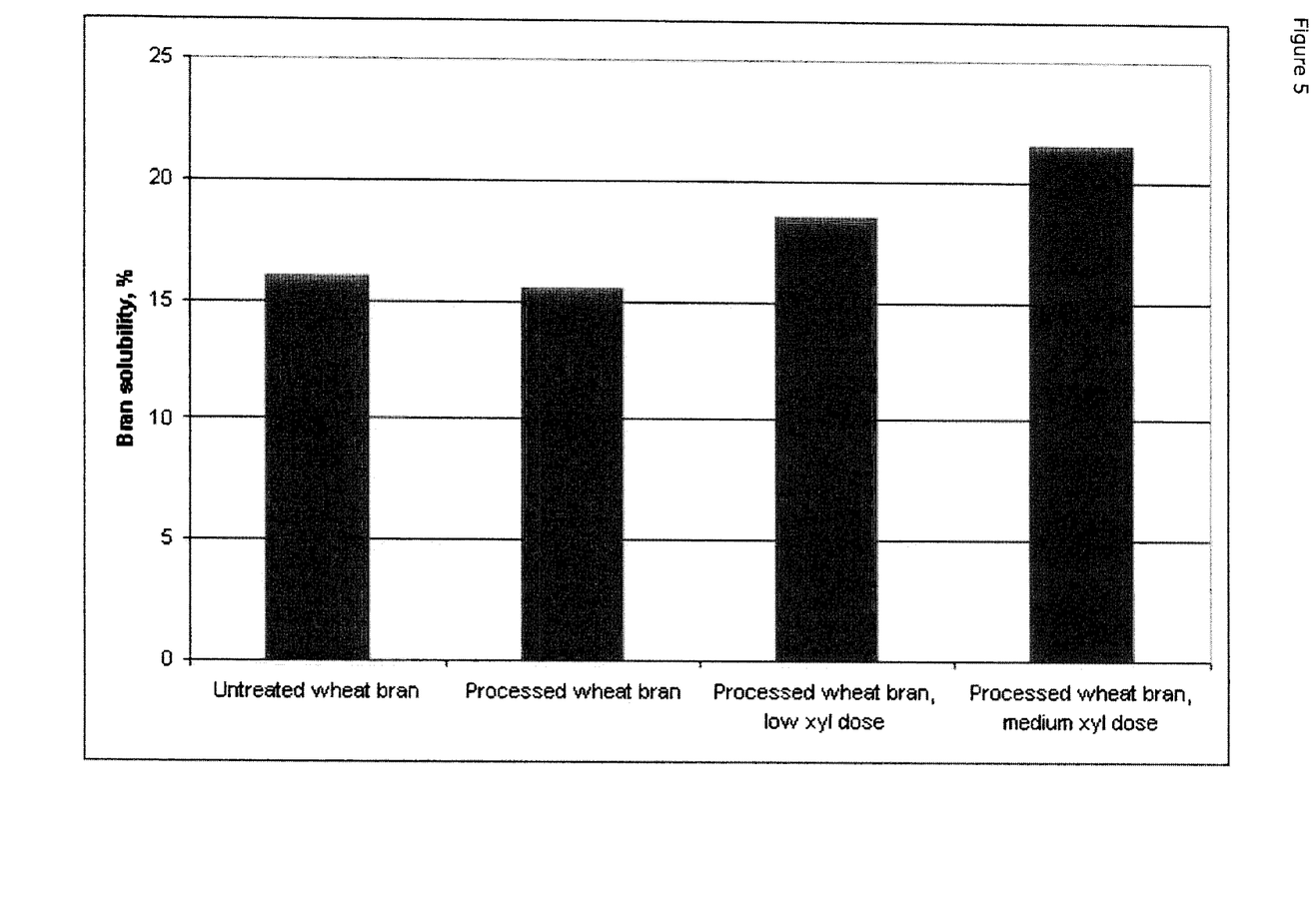
FIG. 5. Bran solubility (%) as a function of bran treatment (Untreated wheat bran, Processed wheat bran without enzyme treatment, Processed wheat bran, low xylanase dose and Processed wheat bran, medium xylanase dose).

Knowing that increasing the solubilisation of the bran material may have huge technological and health & nutritional value, the solubility of the bran treated in different ways was investigated. The solubility of wheat brans treated in different ways is illustrated in FIG. 4 and FIG. 5.

Based on the data, it is clear that the process according to the present invention has a significant effect on the water holding capacity and solubility of cereal brans. The effects differentiate between the two brans tested. The reasons for this are expected to be due to structural differences between the bran cell wall materials or it can be due to different endogenous enzyme concentrations in the samples. Furthermore, it is clear that the process itself, without the addition of enzymes, in case of these brans, has a positive effect on water holding capacity, but a negative on the solubility of the bran. The enzyme treatment has a significant positive effect on the solubilisation of the bran, even though the enzyme treatment was carried out at low moisture content.

The invention claimed is:

1. A method for increasing the water holding capacity (WHC) of a cereal bran fraction, said method comprising the steps of:
    a) adding water to a particulate cereal bran fraction to obtain a water content lower than 100% (w/w); and
    b) treating said particulate cereal bran fraction with added water with one or more xylanases,
    wherein said particulate cereal bran fraction with added water has not been treated to remove any components prior to the treatment in step b),
    wherein the WHC of the cereal bran fraction is increased compared to the WHC of cereal bran not having been treated with one or more xylanases,
    wherein said cereal bran fraction comprises about 20% starch, and
    wherein said components comprise starch.

2. The method of claim 1, wherein the cereal bran fraction is further treated in a heat treatment, wherein the heat treatment reduces enzyme activity, gelatinizes any residual starch, or increases the WHC, when compared to cereal bran not receiving heat treatment.

3. The method of claim 1, wherein the treated cereal bran fraction is solubilised to a degree as determined on drymatter versus drymatter bran higher than 5%.

4. The method of claim 1, wherein the cereal bran fraction is selected from wheat, barley, oat, rye, triticale, rice, and corn.

5. The method according to claim 1, wherein the cereal bran fraction is from a cereal side-stream from processing of plant material.

6. The method of claim 1, wherein said method further comprises one or more of a step of spray drying the treated cereal bran fraction, or a step of lyophilization of the treated cereal bran fraction.

7. The method of claim 1, wherein said cereal bran fraction is treated to obtain a WHC higher than 150% (w/w).

8. The method claim 1, wherein said particulate cereal bran fraction is treated at step b) with one or more xylanases in a concentration ranging from 0.01 mg enzyme protein to 2 mg enzyme protein per kg cereal bran fraction.

9. The method of claim 1, wherein said particulate cereal bran fraction is treated at step b) with one or more xylanases in a period of time in the range from 1-10000 minutes.

10. A method for producing a foodstuff product which comprises utilizing the cereal bran fraction of claim 1, wherein the cereal bran fraction is added in the production of the foodstuff product.

11. The method of claim 10, wherein the foodstuff product is selected from the group consisting of bread, a breakfast cereal, a pasta, biscuits, cookies, snacks, and beer.

12. A kit of parts comprising a) one or more xylanases; and b) instructions for use in a method according to claim 1.

13. The method according to claim 1, further comprising simultaneously or sequentially in any order treating said particulate cereal bran fraction with one or more further enzymes.

14. The kit of parts of claim 12, further comprising:
    one or more further enzymes; and other ingredients for a foodstuff product.

15. The method according to claim 1, wherein the cereal bran fraction is from soap stocks from refining of vegetable oils, brewers spent grain, or Destillers dried spent grain with solubles (DDGS).

* * * * *